(12) United States Patent
Fiere et al.

(10) Patent No.: US 7,172,627 B2  
(45) Date of Patent: Feb. 6, 2007

(54) STABILIZED INTERBODY FUSION SYSTEM FOR VERTEBRAE

(75) Inventors: Vincent Fiere, Lyons (FR); Paul Fayada, Berck (FR); Jean-Paul Taziaux, Rebreuve-Ranchicourt (FR)

(73) Assignee: Scient'X, Guyancourt (FR)

( * ) Notice: Subject to any disclaimer, the term of this patent is extended or adjusted under 35 U.S.C. 154(b) by 0 days.

(21) Appl. No.: 10/473,773

(22) PCT Filed: Apr. 3, 2002

(86) PCT No.: PCT/FR02/01157

§ 371 (c)(1),  
(2), (4) Date: Dec. 28, 2004

(87) PCT Pub. No.: WO02/080819

PCT Pub. Date: Oct. 17, 2002

(65) Prior Publication Data

US 2005/0101960 A1      May 12, 2005

(30) Foreign Application Priority Data

Apr. 3, 2001      (FR) .................................. 01 04489

(51) Int. Cl.  
*A61F 2/44*      (2006.01)

(52) U.S. Cl. .................................................. 623/17.11

(58) Field of Classification Search .. 623/17.11–17.16; 606/61, 69–71  
See application file for complete search history.

(56) References Cited

U.S. PATENT DOCUMENTS

| | | | |
|---|---|---|---|
| 5,709,685 A * | 1/1998 | Dombrowski et al. ........ 606/61 |
| 6,156,037 A * | 12/2000 | LeHuec et al. ................ 606/61 |
| 6,227,149 B1 * | 5/2001 | Host et al. ................... 119/867 |
| 6,235,059 B1 * | 5/2001 | Benezech et al. ......... 623/17.16 |
| 6,306,139 B1 * | 10/2001 | Fuentes ....................... 606/70 |
| 6,576,017 B2 * | 6/2003 | Foley et al. ............. 623/17.16 |
| 6,723,096 B1 * | 4/2004 | Dorchak et al. .............. 606/61 |
| 2002/0107572 A1 * | 8/2002 | Foley et al. ............. 623/17.11 |

FOREIGN PATENT DOCUMENTS

| | | |
|---|---|---|
| EP | 0 974 319 A2 | 1/2000 |
| FR | 2 727 005 A1 | 5/1996 |
| FR | 9813224 | * 10/1998 |
| WO | WO 98/48718 | 11/1998 |
| WO | WO 00/24343 | 5/2000 |

* cited by examiner

Primary Examiner—Eduardo C. Robert  
Assistant Examiner—Michael J. Araj  
(74) Attorney, Agent, or Firm—Clark & Brody

(57) ABSTRACT

The invention concerns a stabilized interbody fusion system for vertebrae, of the type comprising an interbody implant (4) designed to be inserted in the intervertebral space defined between two neighboring vertebrae to be mutually secured, so as to restore the height and the angle of the lordosis of the vertebral segment defined by the two neighboring vertebrae and a stabilizing plate (17) provided, at each of its ends, with at least a passage hole (18) for an anchoring screw, the plate (17) and the implant (4) being provided with mutual assembly means, such that after assembly, the stabilizing plate (17) extends on each side of the implant to enable the stabilizing plate to be anchored on the neighboring vertebrae through the screws, characterized in that it comprises spacing means (30), interposed between the stabilizing plate (17) and the implant (4), to enable the stabilizing plate to be positioned at a specific distance relative to the implant.

19 Claims, 7 Drawing Sheets

STABILIZED INTERBODY FUSION SYSTEM FOR VERTEBRAE

FIELD OF THE INVENTION

The present invention relates to interbody implants to be inserted in the intervertebral space defined between two neighboring vertebrae after intervertebral disk excision, in order to restore the intervertebral space and to form bone fusion between the said neighboring vertebrae.

More precisely, the domain of the invention is lumbar type interbody implants to restore the height and the angle of the lordosis of the vertebral segment defined by two neighboring lumbar vertebrae to be mutually secured.

More precisely, the purpose of the invention is an interbody implant, called a secured implant, in other words provided with the means of anchoring the implant in its insertion site, to prevent it from becoming mobile.

BACKGROUND ART

There are several stabilized interbody fusion systems for vertebrae known in the state of the art. For example, there is a known stabilized system comprising an interbody implant to be inserted in the intervertebral space defined between two neighboring lumbar vertebrae. According to one preferred embodiment, this implant is in the form of a cage comprising two sagittal walls connected to each other through an anterior transverse wall and a posterior transverse wall. The walls delimit a volume between them opening up on each side of the transverse faces of the implant. The open volume of the cage will receive a bone filling product called a bone graft, that will come into contact with the vertebral plates to facilitate bone fusion between the two vertebrae.

This type of stabilized system also comprises a stabilizing plate extending from the anterior wall of the implant and on each side of the transverse faces. This stabilizing plate is provided with passage holes at each of its ends for screws that will be anchored in the vertebrae to be mutually secured.

A stabilizing plate can be placed to reliably prevent migration of the implant. However, the applicant has identified a difficulty in keeping the implant in its ideal position within the intervertebral space to enable it to be anchored on the vertebrae to be mutually assembled through the screws. It must be borne in mind that, in different patients, firstly the anterior edges of the plates of the vertebra bodies have different profiles, and secondly implants are located at different distances from the anterior edges of the plates of the vertebra bodies, that causes displacement of the implant while the stabilizing plate is anchored on the vertebrae.

The applicant expressed the need to have a stabilised interbody fusion system designed firstly so that the implant can be placed in the intervertebral space in an appropriate position to restore a physiological spinal curvature and lordosis, and secondly to hold the implant in this ideal correction position during anchorage of the stabilising plate on the vertebrae, regardless of the shape of the anterior edges of the plates of the vertebra bodies and the position of the implant relative to these anterior edges of the plates.

Therefore, the purpose of the invention is to satisfy this need by proposing a stabilised interbody fusion system capable of restoring the height and the angle of the lordosis of the vertebral segment by an implant, the function of which is secured by a stabilising plate fixed on the vertebrae.

SUMMARY OF THE INVENTION

In order to achieve this objective, the stabilized interbody fusion system for vertebrae according to the invention is of the type comprising:
  an interbody implant that will be inserted in the intervertebral space defined between two neighboring vertebrae to be mutually secured, in order to restore the height and the angle of the lordosis of the vertebral segment defined by two neighboring vertebrae,
  and a stabilizing plate equipped with at least one passage hole for an anchoring screw at each of its ends, the plate and the implant being provided with mutual assembly means such that after assembly, the stabilizing plate extends on each side of the implant to enable the stabilizing plate to be anchored on the neighboring vertebrae through the screws.

The stabilized system comprises spacing means interposed between the stabilizing plate and the implant, to enable the stabilizing plate to be positioned at a specific distance relative to the implant.

BRIEF DESCRIPTION OF THE DRAWINGS

Various other special features will become clear from the description given below with reference to the appended drawings that show example embodiments of the purpose of the invention as non-limitative examples.

DESCRIPTION OF THE PREFERRED EMBODIMENT

Figure 1:
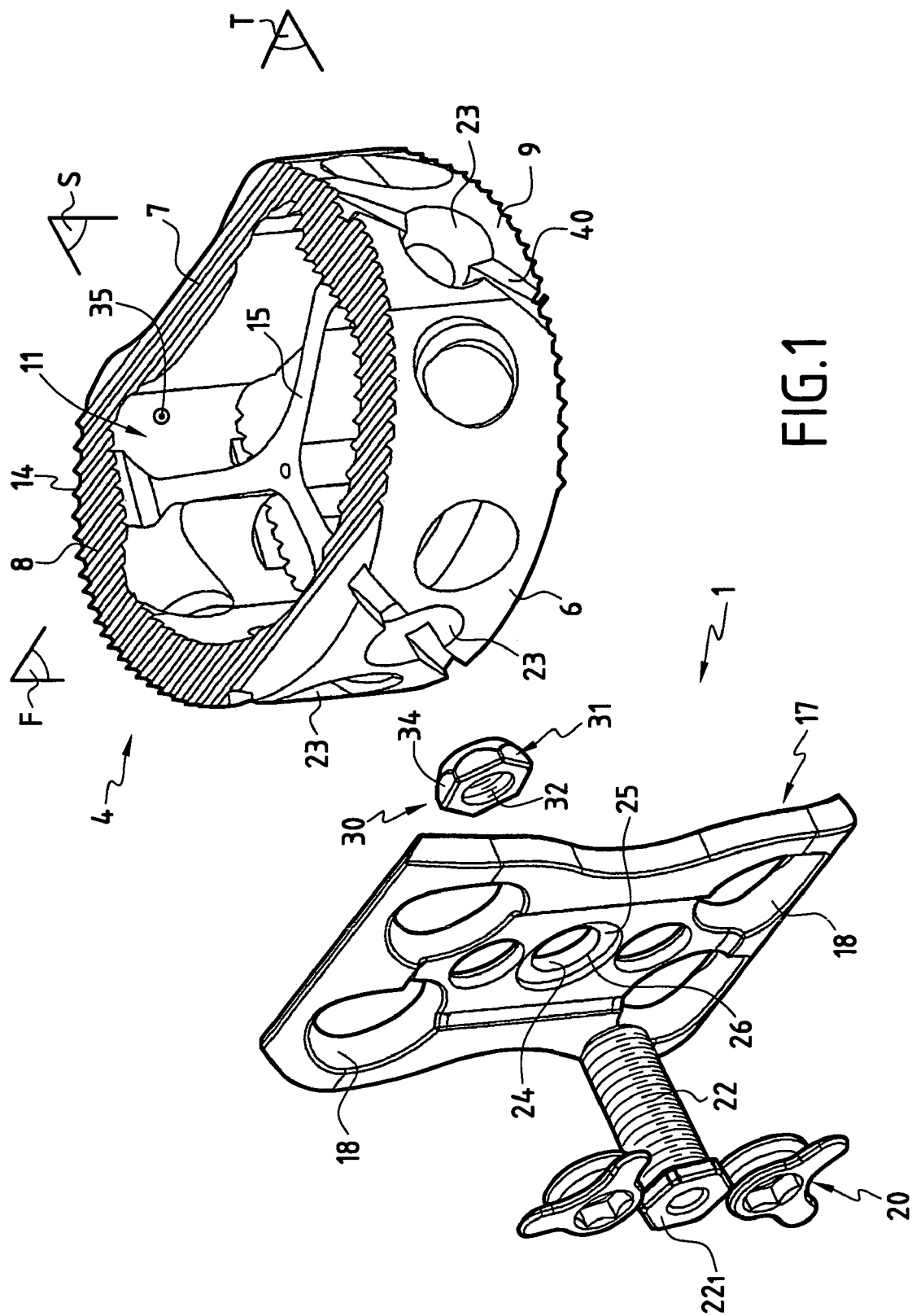
FIG. 1 is an exploded perspective view showing the different constituents of the stabilized system according to the invention.
Figure 2:
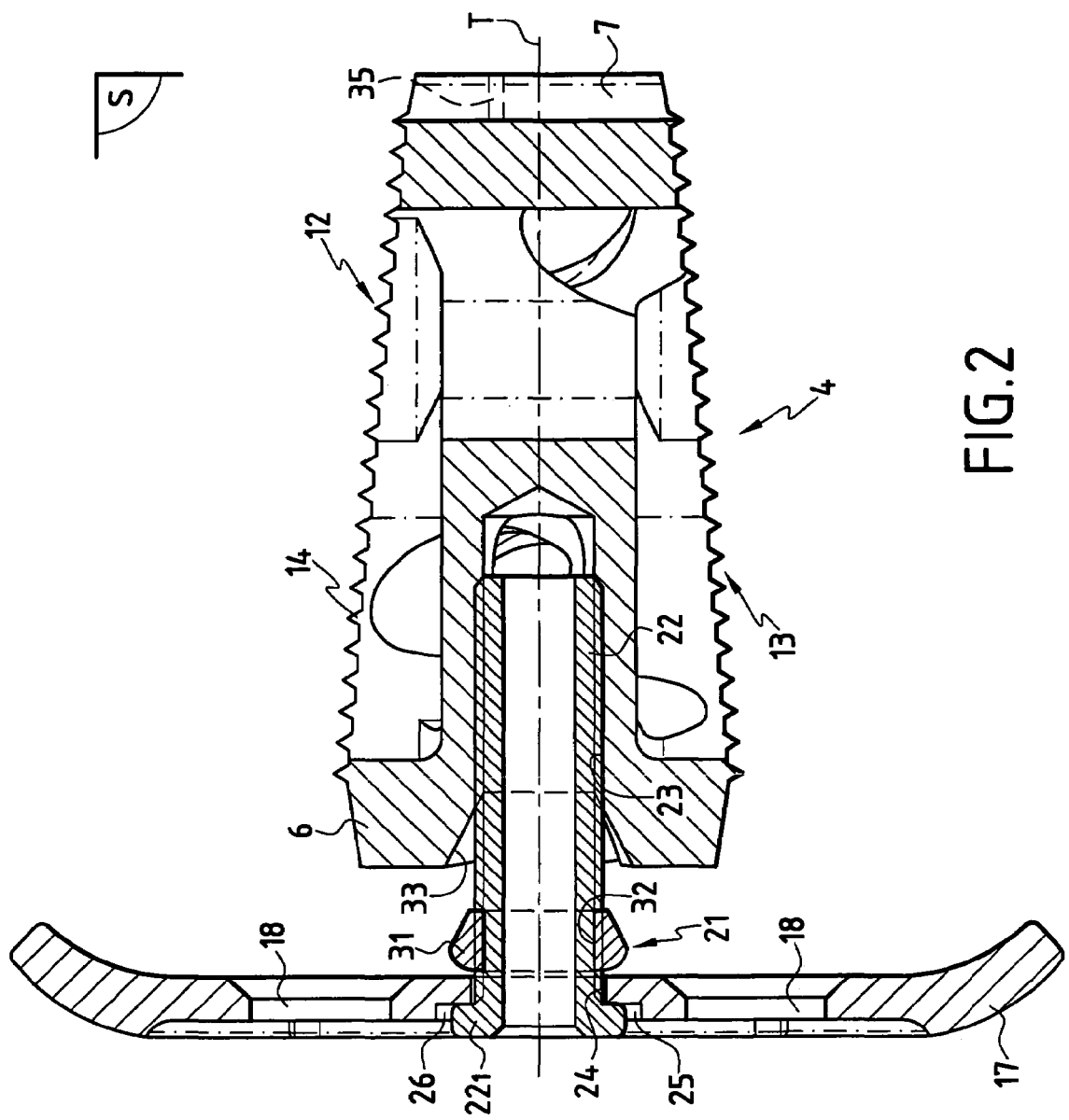
FIG. 2 is a sectional-elevation view of a stabilized system in the raised position.
Figure 3:
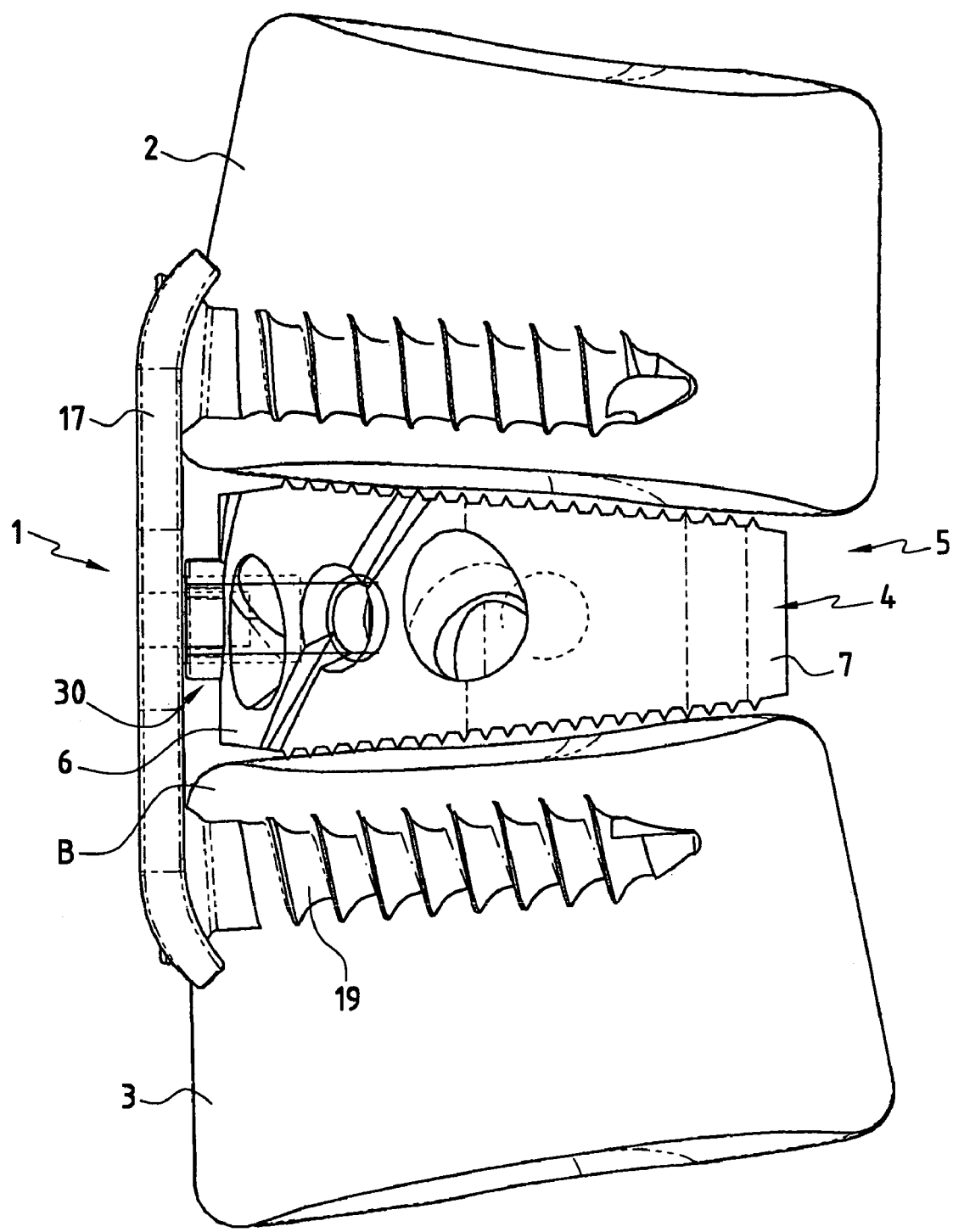
FIG. 3 is an elevation view showing a stabilized system installed on two vertebrae.

As is clear particularly in FIG. 1 to 3, the invention relates to a stabilized interbody fusion system 1 for two neighboring or nearby vertebrae 2, 3. The stabilized system 1 comprises an interbody implant 4 that will be inserted into the intervertebral space 5 delimited by the two vertebrae 2, 3. In one preferred embodiment of the invention as illustrated on the drawings, the implant 4 is made by a cage with a transverse wall 6 called the anterior wall, and a transverse wall 7 called the posterior wall, connected to each other by connecting walls 8, 9. The walls 6 to 9 of the cage are perpendicular to a transverse plane T that is perpendicular to a sagittal plane S passing through the anterior wall 6 and the posterior wall 7. In the transverse plane T, the anterior wall 6 has a convex curvature and extends on each side by the connecting walls 8, 9, which also have convex curvatures and are connected to each other by the posterior wall 7 with a concave curvature to leave the vertebral canal free. The cage 1 thus has a general kidney shape.

As can be seen particularly in FIG. 2, the connecting walls 8, 9 in the sagittal plane S converge towards each other towards the posterior wall 7, such that the cage 1 has a tapered section in the sagittal plane S defining a lordosis correction angle.

The cage 1 comprises an interior volume 11 delimited by interior vertical faces of the walls 6 to 9 and will be filled by a bone filling product called a bone graft adapted to interbody fusion. This volume 11 opens up on a first transverse face 12 called the upper face in the example illustrated, and a second transverse face 13 called the lower face. These transverse faces 12, 13 are delimited by edges of the walls 6 to 9, preferably arranged to comprise notches 14 enabling the cage to be bonded to the superjacent and subjacent vertebrae. The notches 14 extend parallel to each other and from a frontal plane F perpendicular to the sagittal plane S and the transverse plane T.

Preferably, the internal volume 11 of the cage comprises one or several connectors 15 with other walls. In the example illustrated, the connector 15 is in the general shape of a "Y" and extends between the connecting walls 8 and 9 and the anterior wall 6.

The stabilized interbody fusion system 1 conform with the invention also comprises a stabilizing plate 17 for the implant 4. This stabilizing plate 17 is provided with at least one passage hole at each of its ends, and in the example illustrated with two passage holes 18 for the screws 19 that will be anchored on vertebrae 2 and 3 to be mutually secured.

According to one preferred characteristic embodiment, the stabilizing plate 17 is provided with anti-expulsion means 20 for the anchoring screws 19. These anti-expulsion means 20 are composed of moving flaps installed on the stabilizing plate so that they can be guided in rotation in order to occupy a first position in which the passage cross-section of the holes 18 is left free, and a second position in which this passage cross-section is closed off in order to form a stop for the heads of screws 19.

The stabilizing plate 17 and the implant 4 are provided with mutual assembly means 21. The stabilizing plate 17 is adapted so that after assembly with the implant 4, it extends from each side of the transverse faces 12, 13 to the other, to anchor the screws 19 on the vertebrae 2, 3.

According to one characteristic embodiment, the assembly means 21 consist of an assembly screw 22 that will cooperate with at least one threaded hole 23 formed in the implant 4. For example, a threaded hole 23 is arranged to pass through the anterior wall from one side to the other along an axis perpendicular to the anterior wall 6 and centered on the sagittal plane S of symmetry of the implant 4. Preferably, the implant 4 comprises a series of threaded holes 23 to enable assembly of the stabilizing plate 17 in different positions with respect to the implant 4. Thus, a threaded hole 23 is formed in a connecting wall, for example 9, along an axis perpendicular to the axis of the threaded hole 23 formed in the anterior wall 6. At the positions defined by these two threaded holes 23, the stabilizing plate 17 is free to occupy two positions perpendicular to each other. Another threaded hole 23 may also be formed in the other connecting wall, 8, at an angle of 45° C. from the axis of the threaded hole 23 formed in the anterior wall 6.

The assembly screw 22 passes through the stabilizing plate 17 through a passage hole 24, bordered by a stop shoulder 25 formed by a dish 26 arranged to hold the head 221 of the assembly screw 22.

According to one characteristic of the invention, the stabilized device 1 comprises spacing means 30 inserted between the stabilizing plate 17 and the implant 4, to enable the stabilizing plate 17 to be positioned at a specific distance relative to the implant 4. These spacing means 30 fix the stabilizing plate 17 onto the vertebrae leaving the implant 4 in its position, taking account of the shape of the anterior edges B of the plates of vertebrae bodies 2, 3 or the setback position of the implant 4 relative to these anterior edges of the vertebrae.

In the example illustrated in FIG. 1 to 3, the spacing means 30 are composed of a spacer bushing 31 provided with a thread 32 cooperating with the thread of the assembly screw 22. The spacer bushing 31 is thus made in the form of a nut and its outside shape is prismatic and is adapted to cooperate with a part 33 for reception of the implant 4 in which the threaded hole 23 opens up. Cooperation of the spacer bushing 31 with the reception part 33 blocks the bushing 31 in rotation when the assembly screw 22 is being screwed.

Preferably, the reception part 33 is made by an entry cone cooperating with a complementary part 34 presented by the bushing 31. Cooperation of the bushing 31 with the entry cone 33 is a means of adjusting the distance between the stabilising plate 17 and the implant 4.

The stabilized system 1 according to the invention is used directly as a function of the description given above.

Before the implant 4 is inserted, the disc is excised by preparation of the vertebral plates. The implant 4 is implanted in the intervertebral space 5 between two adjacent vertebrae 2 and 3 to be mutually secured. The implant 4 is designed to restore the height and the angle of the lordosis of the vertebral segment defined by the two neighbouring vertebrae 2, 3. The stabilizing plate 17, fitted with its assembly screw 22 provided with its spacer bushing 31, will be installed on the implant 4.

The screw 22 is then screwed into a threaded hole 23 of the implant. The screw 22 is then screwed in until it is fixed in place by the spacer bushing 31 being stopped between the plate 17 and the implant 4. The screws 19 are then anchored in the vertebrae 2, 3.

Obviously, the length of the spacer bushing 31 is adapted to allow the implant 4 to remain in its implantation site, while allowing the stabilizing plate 17 to come into contact with the vertebrae. The stabilizing plate 17 and the implant 4 are separated by a fixed measurement determined by the spacer bushing 31. Preferably, a range of spacer bushings 31 is available. Each of these spacer bushings 31 has a determined length, each of which is different, to adjust the distance between the implant 4 and the stabilizing plate 17.

Note that the implant 4 is preferably provided with at least one radio-opaque element 35 (FIGS. 1 and 2) adapted so that the position of the implant 4 within the intervertebral space 5 along the sagittal plane S can be detected on an X-ray. In the example illustrated, the radio-opaque element 35 is installed in the posterior wall 7 extending in the transverse plane and opening up on the external face and the internal face of the posterior wall 7.

Figure 4:
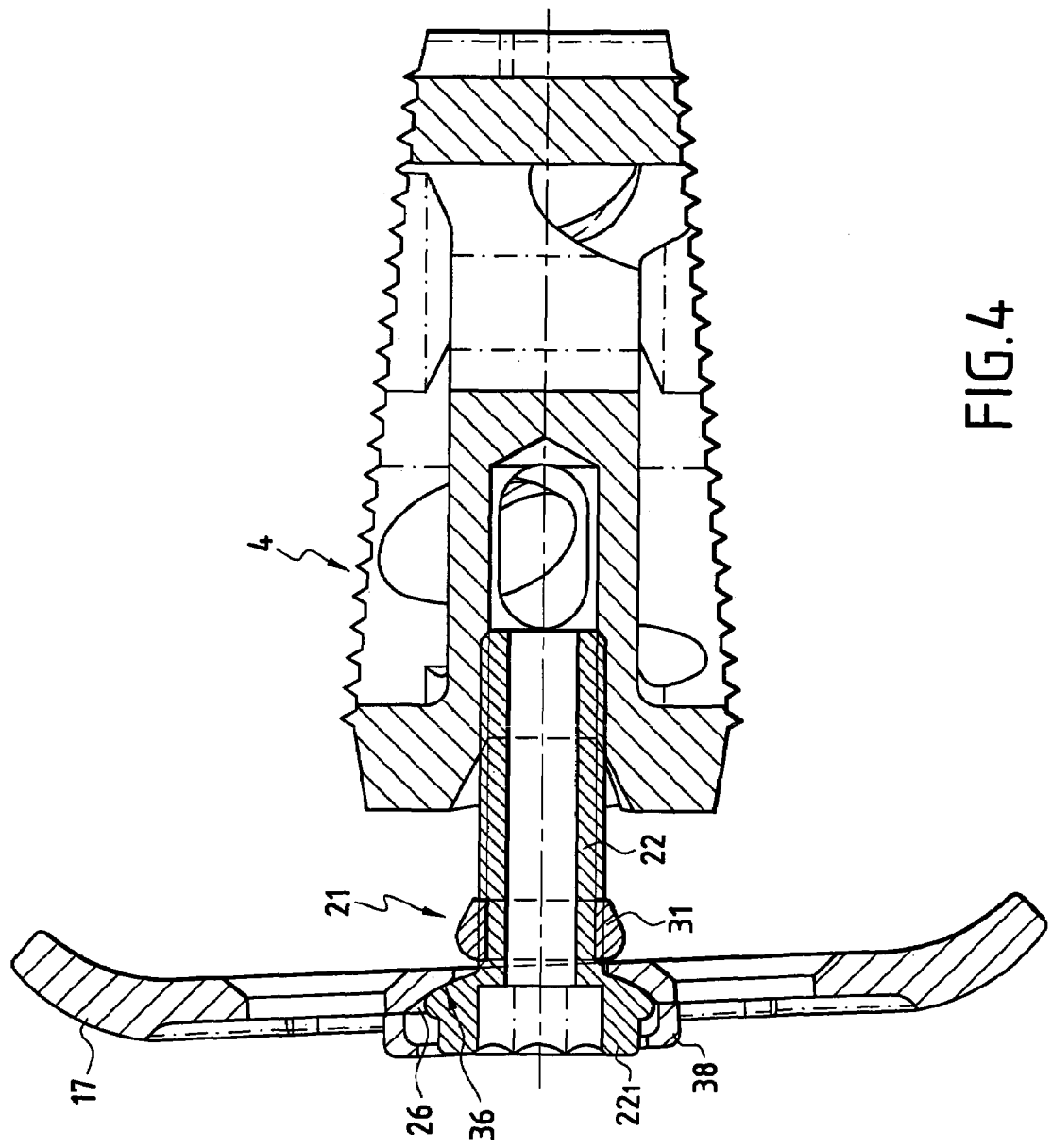
FIG. 4 is a sectional-elevation view showing another variant embodiment of the stabilized system according to the invention.

According to one example embodiment illustrated in FIG. 4, the assembly means 21 are provided with support means 36 for the stabilizing plate 17 allowing angular orientation of the stabilizing plate relative to the implant 4. For example, these support means 36 may be made by a ball joint type articulation formed between the head 221 of the assembly screw 22 and the dish 26 in the plate 17. In this variant embodiment illustrated, the screw 22 is assembled to the stabilizing plate 17 using a ring 38 fixed on the plate 17 to trap the head 221 of the screw 22, while allowing the screw 22 free to rotate about its own axis.

Figure 5:
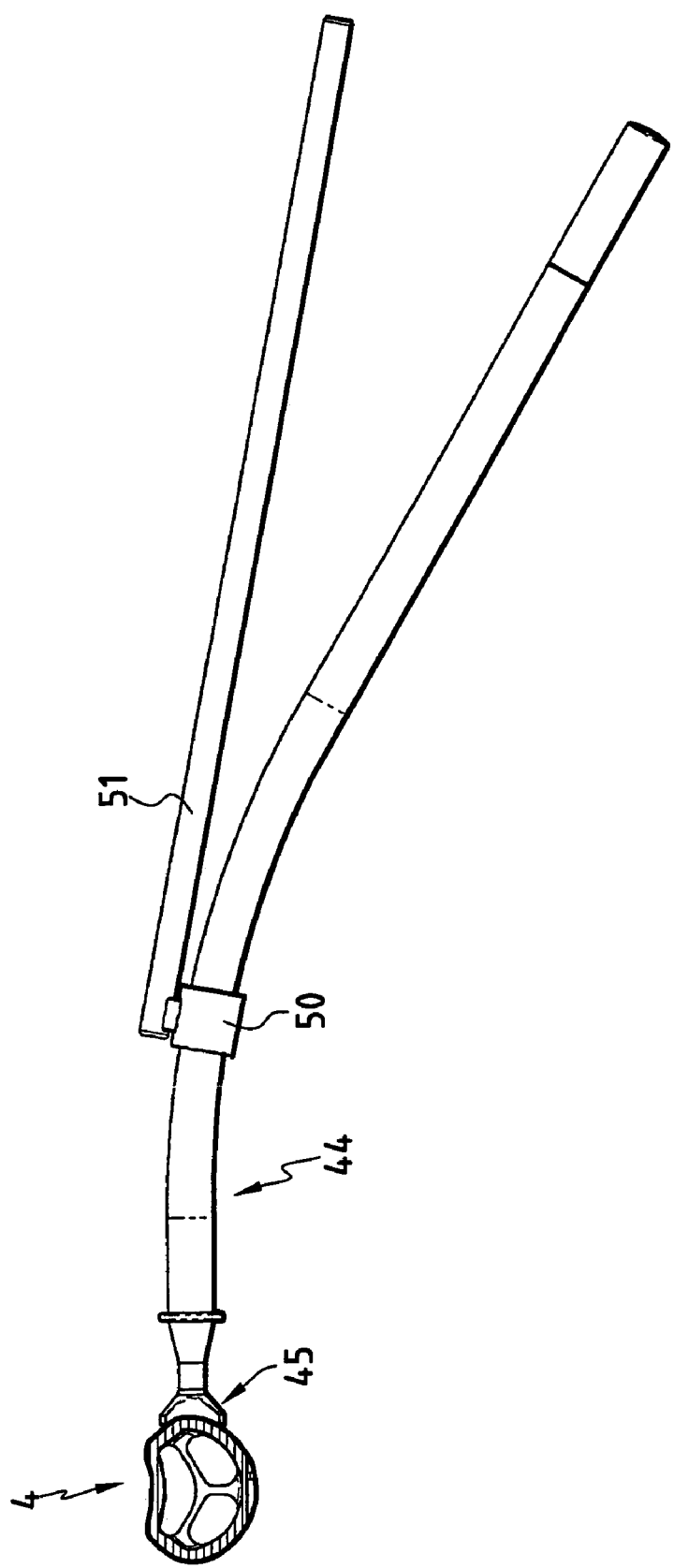
FIGS. 5 and 6 are perspective views showing characteristic details of a gripping instrument for an implant according to the invention.
Figure 6:
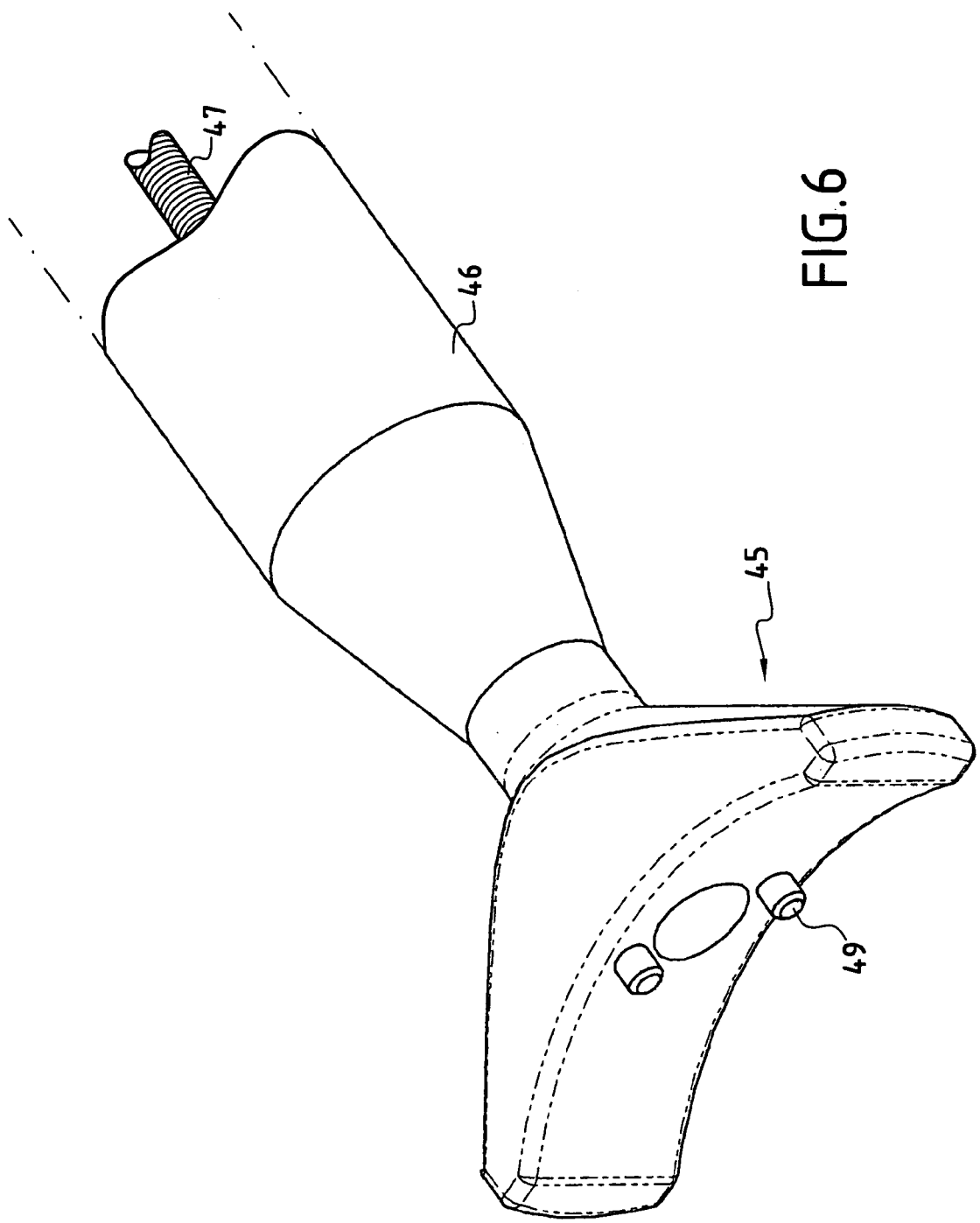

According to one preferred variant embodiment, each threaded hole 23 of the implant is surrounded by an assembly groove 40, inclined relative to the sagittal plane and designed to cooperate with a gripping or manipulation instrument 44 for use on the implant 4. As can be seen in FIGS. 5 and 6, the manipulation instrument 44 comprises an assembly head 45 prolonged by a maneuvering tube 46 inside which a flexible threaded rod 47 passing through the head 45 is installed, so as to cooperate with a threaded hole 23 in the implant. The assembly head 45 is provided with two dog pins 49 that will be inserted in the groove 40 on each side of the threaded hole 23. The instrument 44 thus enables complete gripping and blocking of the implant 4 with respect to the assembly head 45.

According to one preferred variant embodiment, the maneuvering tube 46 has a curvature and is provided with a slide 50 on which there is a bar 51, the free end of which is adapted to resist forces for placement of the implant and to ensure that the approach is respected.

In the above description, the stabilised interbody fusion system 1 comprises an implant 4 made in the form of a generally parallelepiped shaped cage. Obviously, the purpose of the invention could be used for an interbody implant in the form of a cylindrical or semi-cylindrical cage.

Figure 7:
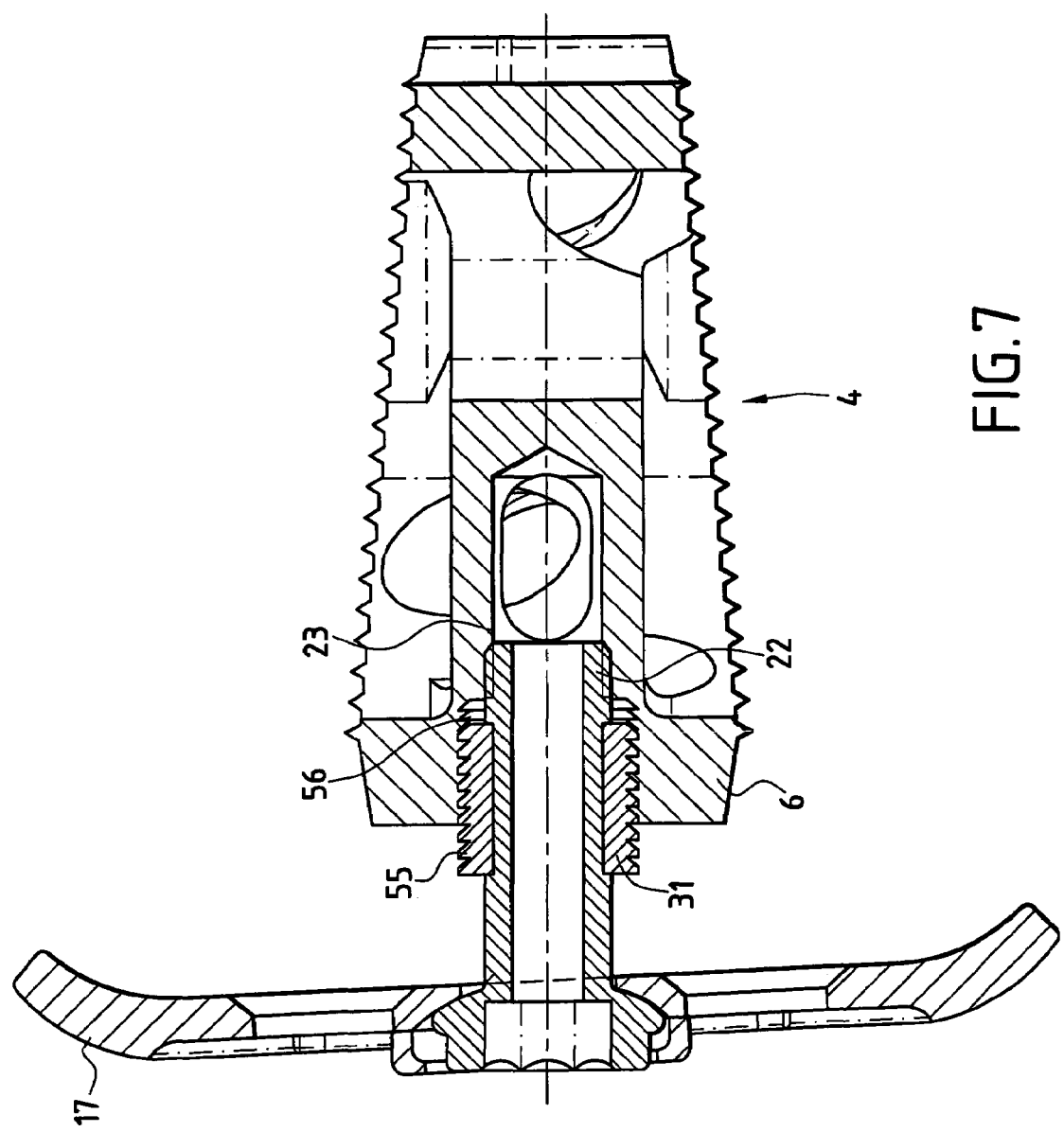
FIG. 7 is a sectional-elevation view illustrating another variant embodiment of a stabilized system according to the invention.

In the above description, the spacer bushing 31 is put into place during assembly of the stabilizing plate 17 on the implant 4, while being carried by the assembly screw 22. Obviously, it will be possible for the spacer means 30 to be fixed onto the stabilizing plate 17. Similarly, figure 7 illustrates another variant embodiment of the invention in which the spacer bushing 31 is fixed to the implant 4 before the operation. This spacer bushing 31 comprises assembly means 55 on the implant, for example made of notches cooperating with complementary notches 56 formed on the anterior wall 6, and into which the threaded hole 23 opens up. Therefore this spacer bushing 31 can then be installed on the implant 4 with the possibility of adjusting its degree of penetration, so that the distance between the implant 4 and the stabilizing plate 17 can thus be adjusted. Preferably, this spacer bushing 31 is split along its length so as to block its position during assembly of the assembly screw 22 that passes through this bushing 31, to be screwed into the threaded hole 23.

The invention is not limited to the examples described and illustrated since many modifications can be made without departing from its scope.

The invention claimed is:

1. Stabilized interbody fusion system for vertebrae according to the invention, of the type comprising:

an interbody implant that will be inserted in the intervertebral space defined between two neighboring vertebrae to be mutually secured therebetween, in order to restore the height and the angle of the lordosis of the vertebral segment defined by two neighboring vertebrae; and a stabilizing plate equipped with at least one passage hole for an anchoring screw at each of its ends, and a top surface and a bottom surface, the plate and the implant being provided with mutual assembly means such that after assembly, the stabilizing plate extends on each side of the implant to enable the stabilizing plate to be anchored on the neighboring vertebrae through the screws, wherein the assembly means comprises spacing means having a top surface in contact with the bottom surface of the stabilizing plate so that the spacing means is interposed between the bottom surface of the stabilizing plate and an outer surface of the implant, to enable the stabilizing plate to be positioned at a specific distance relative to the outer surface of the implant.

2. According to claim 1, wherein the spacing means adjust the distance between the stabilizing plate and the implant.

3. System according to claim 2, wherein the assembly means are provided with support means for the plate allowing angular orientation of the plate relative to the implant.

4. System according to claim 2, wherein the spacing means comprises at least one spacer bushing.

5. System according to claim 1, wherein the spacing means are chosen from among a range of spacing means each with a determined length, each of which is different, to adjust the distance between the plate and the implant at a value that is determined by the length of the chosen spacing means.

6. System according to claim 5, wherein the assembly means are provided with support means for the plate allowing angular orientation of the plate relative to the implant.

7. System according to claim 5, wherein the spacing means comprises at least one spacer bushing.

8. System according to claim 1, wherein the assembly means are provided with support means for the plate allowing angular orientation of the plate relative to the implant.

9. System according to claim 8, wherein the spacing means comprises at least one spacer bushing.

10. System according to claim 1, wherein the spacing means comprises at least one spacer bushing.

11. System according to claim 10, wherein the spacer bushing is fixed to the stabilizing plate.

12. System according to claim 11, wherein the spacer bushing comprises assembly means on the implant, allowing adjustment of the distance between the stabilizing plate and the implant.

13. System according to claim 11, wherein the spacer bushing is put into place on an assembly screw forming part of the assembly means and is designed to pass through the plate through a passage hole bordered by a stop shoulder arranged to hold the head of the assembly screw and to cooperate with at least one threaded hole arranged in the implant.

14. System according to claim 13, wherein the threaded hole is formed on the anterior wall of the implant, this wall having a convex curvature in the transverse plane and extending by connecting walls with a convex curvature, to a posterior wall with a concave curvature to leave the vertebral canal free.

15. System according to claim 14, wherein each connecting wall is arranged to contain a threaded hole surrounded, like the threaded hole formed in the anterior wall, by an assembly groove designed to cooperate with two assembly dog pins provided on the head of a gripping instrument of the implant, also comprising a threaded rod designed to cooperate with a threaded hole in the implant.

16. System according to claim 14, wherein the posterior wall is fitted with a radio-opaque element opening up on the external face of the said wall, adapted so that the position of the implant within the intervertebral space along the sagittal plane can be detected.

17. System according to claim 1, wherein the stabilizing plate is provided with anti-expulsion means for the anchoring screws, installed on the plate through moving guide means and adapted to occupy a first position in which the passage cross-section of the holes for reception of the anchoring screws is left free, and a second position, in which the holes are partially closed off, in order to form a stop for the heads of screws.

18. A gripping instrument, comprising:
a maneuvering tube, inside which a flexible threaded rod is fitted so as to cooperate with a threaded hole in the implant of claim 1, the tube further comprising an assembly head, fitted with two dog pins to cooperate with an assembly groove surrounding the treaded hole.

19. The gripping instrument according to claim 18, wherein the maneuvering tube on the implant has a curvature and is provided with a slide on which there is a bar, the free end of which is adapted to resist forces for placement of the implant and to ensure that the approach is respected.

* * * * *